US010370789B2

(12) United States Patent
Gedanken et al.

(10) Patent No.: US 10,370,789 B2
(45) Date of Patent: *Aug. 6, 2019

(54) SONOCHEMICAL COATING OF TEXTILES WITH METAL OXIDE NANOPARTICLES FOR ANTIMICROBIAL FABRICS

(71) Applicant: BAR ILAN UNIVERSITY, Ramat Gan (IL)

(72) Inventors: Aharon Gedanken, Givataim (IL); Yeshayahu Nitzan, Givat Shmuel (IL); Ilana Perelshtein, Rishon le Zion (IL); Nina Perkas, Petach Tikva (IL); Guy Applerot, Ramat Gan (IL)

(73) Assignee: BAR ILAN UNIVERSITY, Ramat Gan (IL)

( * ) Notice: Subject to any disclaimer, the term of this patent is extended or adjusted under 35 U.S.C. 154(b) by 374 days.

This patent is subject to a terminal disclaimer.

(21) Appl. No.: 15/132,042

(22) Filed: Apr. 18, 2016

(65) Prior Publication Data
US 2016/0302420 A1  Oct. 20, 2016

Related U.S. Application Data

(63) Continuation-in-part of application No. 12/997,276, filed as application No. PCT/IL2009/000645 on Jun. 29, 2009, now Pat. No. 9,315,937.
(Continued)

(51) Int. Cl.
*A61K 9/00* (2006.01)
*A61K 9/06* (2006.01)
(Continued)

(52) U.S. Cl.
CPC ............ *D06M 10/02* (2013.01); *A01N 25/10* (2013.01); *A01N 25/34* (2013.01); *A61K 9/0014* (2013.01);
(Continued)

(58) Field of Classification Search
CPC .... C08F 2/56; G03G 9/08; A61K 9/70; B32B 27/14
See application file for complete search history.

(56) References Cited

U.S. PATENT DOCUMENTS

| 4,207,071 A | 6/1980 | Lipowitz et al. |
| 5,466,722 A * | 11/1995 | Stoffer ................... B01J 19/10 |
| | | 522/168 |

(Continued)

FOREIGN PATENT DOCUMENTS

| CN | 1807750 A | 7/2006 |
| IL | WO2007032001 A2 | 3/2006 |

(Continued)

OTHER PUBLICATIONS

Espace Translation of WO2007/058297 in English (Year: 2007).*
(Continued)

*Primary Examiner* — Gregory R Delcotto
*Assistant Examiner* — Preeti Kumar
(74) *Attorney, Agent, or Firm* — Symbus Law Group, LLC; Clifford D. Hyra

(57) ABSTRACT

We disclose a system for preparing antimicrobial surfaces, coated with metal oxide nanoparticles by means of a novel sonochemical method. These antibacterial surfaces are widely used in medical and other applications. The deposition of metal oxides known to possess antimicrobial activity, namely ZnO, MgO and CuO, can significantly extend the applications of textile fabrics, medical devices and other items and prolong the period of their use. By means of the novel sonochemical method disclosed here, uniform deposition of metal oxide nanoparticles is achieved simply.

22 Claims, 6 Drawing Sheets

Related U.S. Application Data

(60) Provisional application No. 61/129,472, filed on Jun. 30, 2008.

(51) Int. Cl.

| | |
|---|---|
| *A61K 9/51* | (2006.01) |
| *B05D 1/00* | (2006.01) |
| *A01N 25/10* | (2006.01) |
| *A01N 25/34* | (2006.01) |
| *A01N 59/16* | (2006.01) |
| *A01N 59/20* | (2006.01) |
| *A61K 33/08* | (2006.01) |
| *A61K 33/30* | (2006.01) |
| *A61K 33/34* | (2006.01) |
| *A61L 15/46* | (2006.01) |
| *C23C 18/14* | (2006.01) |
| *D06M 10/02* | (2006.01) |
| *D06M 10/06* | (2006.01) |
| *D06M 10/08* | (2006.01) |
| *D06M 11/36* | (2006.01) |
| *D06M 11/44* | (2006.01) |
| *D06M 11/49* | (2006.01) |
| *D06M 23/08* | (2006.01) |

(52) U.S. Cl.
CPC .............. *A61K 9/06* (2013.01); *A61K 9/5115* (2013.01); *A61K 33/08* (2013.01); *A61K 33/30* (2013.01); *A61K 33/34* (2013.01); *A61L 15/46* (2013.01); *B05D 1/00* (2013.01); *C23C 18/14* (2013.01); *D06M 10/06* (2013.01); *D06M 10/08* (2013.01); *D06M 11/36* (2013.01); *D06M 23/08* (2013.01); *A61L 2300/102* (2013.01); *D06M 11/44* (2013.01); *D06M 11/49* (2013.01)

(56) References Cited

U.S. PATENT DOCUMENTS

| | | | |
|---|---|---|---|
| 5,656,037 A | 8/1997 | Vigo et al. | |
| 7,824,768 B2 | 11/2010 | Shan et al. | |
| 8,133,932 B2 * | 3/2012 | Kijlstra | B01J 13/0043 106/1.05 |
| 9,315,937 B2 * | 4/2016 | Gedanken | D06M 11/42 |
| 2003/0017336 A1 | 1/2003 | Gedanken et al. | |
| 2005/0085144 A1 | 4/2005 | MacDonald et al. | |
| 2006/0021642 A1 | 2/2006 | Sliwa, Jr. et al. | |
| 2006/0141015 A1 * | 6/2006 | Tessier | A01N 59/16 424/443 |
| 2007/0054577 A1 | 3/2007 | Avloni | |
| 2009/0162636 A1 * | 6/2009 | Shan | B82Y 30/00 428/323 |
| 2010/0035047 A1 * | 2/2010 | Ajayan | C08J 3/20 428/328 |

FOREIGN PATENT DOCUMENTS

| | | | | |
|---|---|---|---|---|
| JP | WO2007058297 A1 | 5/2007 | | |
| WO | WO-2007058297 A1 * | 5/2007 | ............. | B82Y 30/00 |
| WO | WO-2007118669 A1 * | 10/2007 | .......... | B01J 13/0043 |

OTHER PUBLICATIONS

International Search Report dated Nov. 13, 2009 issued in application PCT/IL2009/000645.
Non-final Office Action issued in U.S. Appl. No. 12/997,276 dated Mar. 5, 2013.
Final office action issued in U.S. Appl. No. 12/997,276 dated Aug. 16, 2013.
Non-Final office action issued in U.S. Appl. No. 12/997,276 dated Apr. 11, 2014.
Final office action issued in U.S. Appl. No. 12/997,276 dated Aug. 8, 2014.
Non-Final office action issued in U.S. Appl. No. 12/997,276 dated May 22, 2015.
EP Search report issued in EP09773041.0dated Feb. 24, 2015.
Notice of Allowance issued in U.S. Appl. No. 12/997,276 dated Dec. 31, 2015.
Examination report issued in EP09773041.0 dated Feb. 24, 2015.
Examination report issued in EP09773041.0 dated Jun. 15, 2015.
Examination report issued in EP09773041.0 dated Jan. 22, 2016.
Intention to Grant issued in EP09773041.0 dated Jun. 14, 2016.

* cited by examiner

SONOCHEMICAL COATING OF TEXTILES WITH METAL OXIDE NANOPARTICLES FOR ANTIMICROBIAL FABRICS

This application is a continuation-in-part of and claims priority to U.S. patent application Ser. No. 12/997,276, filed Dec. 10, 2010, which is a national stage entry of PCT application PCT/IL09/00645, filed Jun. 29, 2009, which is a nonprovisional of U.S. provisional patent application 61/129,472, filed Jun. 30, 2008, all of which are hereby incorporated by reference in their entireties.

FIELD OF THE INVENTION

The present invention relates to a system for preparing antimicrobial surfaces, coated with metal oxide nanoparticles by a novel sonochemical method.

BACKGROUND OF THE INVENTION

Antibacterial fabrics are widely used for production of outdoor clothes, under-wear, bed-linen, and bandages. Antimicrobial resistance is very important in textile materials, having effects amongst others on comfort for the wearer. The deposition of metal oxides known to possess antimicrobial activity, namely ZnO, MgO and CuO, can significantly extent the applications of textile fabrics and prolong the period of their use.

Zinc oxide has been recognized as a mild antimicrobial agent, non toxic wound healing agent, and sunscreen agent. Because it reflects both UVA and UVB rays, zinc oxide can be used in ointments, creams and lotions to protect against sunburn and other damage to the skin caused by ultraviolet lights [Godfrey H. R. Alternative Therapy Health Medicine, 7 (2001) 49]. At the same time ZnO is an inorganic oxide stable against temperatures encountered in normal textile use, contributing to its long functional lifetime without color change or oxidation. The antibacterial properties of MgO and CuO nanoparticles were also demonstrated [*Controllable preparation of Nano-MgO and investigation of its bactericidal properties*. Huang L., Li D. Q, Lin Y. J., Wei M., Evans D. G., Duan X. L. Inorganic Biochemistry, 99 (2005) 986, and *Antibacterial Vermiculite Nano-Material*. Li B., Yu S., Hwang J. Y., Shi S. Journal of Minerals & Materials Characterization & Engineering, 1 (2002) 61].

An antimicrobial formulation containing ZnO powder, binding agent, and dispersing agent was used to protect cotton and cotton-polyester fabrics ["Microbial Detection, Surface Morphology, and Thermal Stability of Cotton and Cotton/Polyester Fabrics Treated with Antimicrobial Formulations by a Radiation Method". Zohby M. H., Kareem H. A., El-Naggar A. M., Hassan, M. S., J. Appl. Polym. Sci. 89 (2003) 2604] This formulation was applied to fabrics under high energy radiation of Co-60 γ or electron beam irradiation and then subjected for fixation by thermal treatment. A superior antimicrobial finish was achieved with cotton fabrics containing 2 wt % ZnO and with cotton-polyester fabrics containing 1 wt % ZnO. The particle size of ZnO in these samples according to SEM measurement was 3-5 μm. In spite of good antimicrobial activity, the disadvantages of this method are the use of additional binding and dispersing agent, and requirements of high energy radiation and an additional stage of thermal curing. It was also reported that ZnO-soluble starch nanocomposite was impregnated onto cotton fabrics to impart antibacterial and UV-protection functions with ZnO concentration 0.6-0.8 wt % [*Functional finishing of cotton fabrics using zinc oxide-soluble starch nanocomposites*. Vigneshwaran N., Kumar S., Kathe A. A., Varadarajan P., Prasad V., Nanotechnology 17 (2006) 5087]. The particle size of ZnO in zinc oxide-starch composition was reported as 38 nm. However, in this work the special stabilizing agent, namely, acrylic binder is used which should undergo the additional stage of polymerization at 140° C.

Improved methods of producing metal oxide nanoparticles and coating them onto surfaces is still a long felt need.

BRIEF DESCRIPTION OF THE DRAWINGS

In order to understand the invention and to see how it may be implemented in practice, a plurality of embodiments will now be described, by way of non-limiting example only, with reference to the accompanying drawings, in which.

SUMMARY OF THE INVENTION

Figure 1:
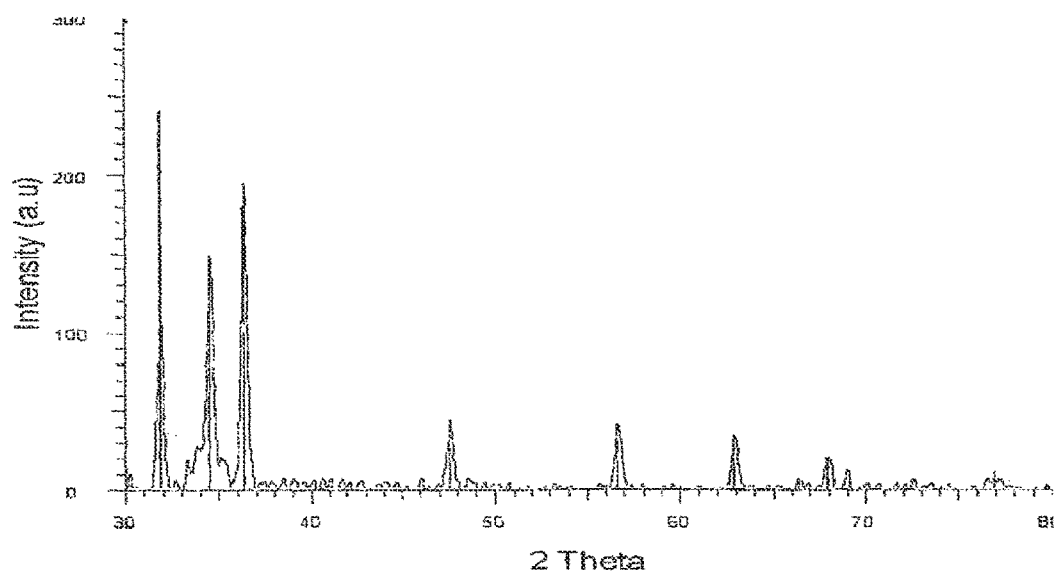
FIG. 1 presents an XRD pattern indicating hexagonal phase of ZnO matching PDF file: 89-7102.

The present invention comprises systems and methods for sonochemical production and dispersion of metal oxide nanoparticles onto surfaces.

A sonication-assisted reaction is conducted "in situ", i.e. in the presence of a corresponding substrate. Ultrasonic waves are produced by acoustic bubbles formed by ultrasonic radiation, which tend to collapse preferentially near solid surfaces. The after-effects of the collapse are microjets and shock waves directed towards the solid surfaces. NPs formed during the collapse of the ultrasonic bubbles near surfaces are thrown at these surfaces by the microjets. As a result, the NPs are strongly anchored to the substrate/surface without the use of any binding agent. Use of such a one-stage sonication procedure shortens preparation time and is inexpensive, not requiring complicated equipment since it is carried out in chemical solution by controlling concentration of reagents and reaction time.

A new method for ultrasonic impregnation of various surfaces with metal oxide nanoparticles consists of steps of:
  a. preparing a water ethanol solution;
  b. adding $M(Ac)_2$ to said solution, forming a mixture;
  c. immersing said surface in said mixture;
  d. adjusting the pH of said mixture to basic pH by means of addition of aqueous ammonia;
  e. purging said mixture to remove traces of $CO_2$/air;
  f. irradiating said mixture with a high intensity ultrasonic power;
  g. washing said surface with water to remove traces of ammonia;
  h. further washing said surface with ethanol, and drying in air.

thereby producing a surface-metal oxide composite containing homogeneously impregnated metal oxide nanoparticles, without use of electromagnetic radiation. The surface may be any type of material, including ceramics, polymers, metals, glass, textile and/or paper. Depending on permeability of the material, deposited NPs may end up only on the outer surface of the material (e.g. for metal surfaces) or penetrating to some extent into the interior of the material, for example nanoparticles may soak into some or all fibers of a textile. The method is especially useful for applications where antibacterial and/or antifungal properties are desirable, for example with medical devices such as catheters, contact lenses, even surgical instruments.

In some embodiments, known methods other than addition of ammonia may be used to adjust pH of the mixture.

In some embodiments, solvents other than ethanol may be used instead of or in addition to ethanol in preparing the solution. A number of different solutions may be used, depending on the application and particulars of the other steps of the process.

It is further within provision of the invention to provide the aforementioned method where said water-ethanol solution is in a ratio of approximately 1:9.

It is further within provision of the invention to provide the aforementioned method where $M(Ac)_2$ is added in a concentration of between 0.002 and 0.2 M.

It is further within provision of the invention to provide the aforementioned method where M is selected from a group consisting of metals Zn, Mg, Cu.

It is further within provision of the invention to provide the aforementioned method where said basic pH is approximately 8.

It is further within provision of the invention to provide the aforementioned method where said step of purging is carried out with argon for 1 hour.

It is further within provision of the invention to provide the aforementioned method where said step of irradiating said mixture is carried out for 1 hour It is further within provision of the invention to provide the aforementioned method where said step of irradiating said mixture is carried out by means of an ultrasonic horn It is further within provision of the invention to provide the aforementioned method where said step of irradiating said mixture is carried out using ultrasonic waves at a frequency of approximately 20 kHz.

It is further within provision of the invention to provide the aforementioned method where said step of irradiating said mixture is carried out using ultrasonic waves at a power of approximately 1.5 kW It is further within provision of the invention to provide the aforementioned method where said step of irradiating said mixture is carried out under a flow of argon It is further within provision of the invention to provide the aforementioned method where said step of irradiating said mixture is carried out at approximately 30° C.

It is further within provision of the invention to provide the aforementioned method where said textile composite contains between 0.1 wt % and 10 wt % of metal oxide (MO).

It is further within provision of the invention to provide the aforementioned method where MO nanocrystals are between 10 nm and 1000 nm in diameter.

It is further within provision of the invention to provide textiles imparted with bacteriostatic properties by means of ultrasonic irradiation of said textiles in an aqueous metal oxide mixture, thereby attaining uniform impregnation of said textiles with metal oxide nanoparticles.

Another new method for ultrasonic impregnation of various surfaces with metal oxide nanoparticles consists of steps of:
a. adding M(Ac)2 to water, forming a mixture;
b. immersing said surface in said mixture;
c. adjusting the pH of said mixture to basic pH by means of addition of aqueous ammonia;
d. purging said mixture to remove traces of CO2/air;
e. irradiating said mixture with a high intensity ultrasonic power;
f. washing said surface with water to remove traces of ammonia;
g. further washing said surface with ethanol, and drying in air.

thereby producing a surface-metal oxide composite containing homogeneously impregnated metal oxide nanoparticles, without use of electromagnetic radiation.

Step d is optional, and good results are obtained even without it.

The above water-based reaction may be used for simultaneous production of NPs and coating of various substrates with the antibacterial metal oxide NPs. In a one-step reaction, the water solution of corresponding metal ($Zn^{+2}$ or $Cu^{+2}$) undergoes a hydrolysis process in a basic environment (pH~8).

Performing the method without steps b and f-g may be used to produce NPs without applying them to a surface, while steps b-g may be used with an additional step of adding NPs to the mixture to coat surfaces with NPs without simultaneously producing the NPs.

As before, the surface may be any type of material, including ceramics, polymers, metals, glass, textile and/or paper and applications include medical devices, etc.

By avoiding the use of ethanol in the mixture, potential toxicity of NPs due to the use of ethanol during the synthesis process and its aggregation during interaction with cells can be avoided. Fires and other accidents during bulk scale NP synthesis may also be prevented, and the process may also be more economical (water is typically cheaper than ethanol and the resulting process is less complex) and more environmentally-friendly (without the need to dispose of ethanol waste).

NPs synthesized in water have different shape and size characteristics than those synthesized in water-ethanol solutions, however functionality of coatings of the NPs are unaffected by these variations in size and shape. Additionally, Mg-based NPs are not effectively synthesized in water alone, although Zn and Cu-based NPs are. The water-based method may still be used for applying Mg-based NPs (e.g. obtained commercially) to surface.

According to another embodiment of the present invention, when commercial nanoparticles, or nanoparticles otherwise produced by means other than sonochemically, are introduced in the sonication mixture, the ultrasound can still be used for "throwing stones" at the surface, and good antibacterial properties (when antibacterial nanoparticles, such as MO nanoparticles, are used) are obtained. Either of the above methods may be modified to replace step a. with a step of adding commercial/pre-made MO (or other) nanoparticles to the water or water-ethanol solution, or the pre-made NP may be added as an additional step. While the invention is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF PREFERRED EMBODIMENTS

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a means and method for providing a wood-resin composite.

In the following detailed description, numerous specific details are set forth in order to provide a thorough understanding of embodiments of the present invention. However, those skilled in the art will understand that such embodiments may be practiced without these specific details. Reference throughout this specification to "one embodiment" or "an embodiment" means that a particular feature, structure, or characteristic described in connection with the embodiment is included in at least one embodiment of the invention.

The term 'sonochemical irradiation' hereinafter refers to exposure to sonic power, generally in the ultrasonic range of frequencies.

The term 'sonochemistry' refers to the study or use of sonochemical irradiation.

The term 'nanoparticles' hereinafter refers to particles of size ranging from about micrometers to about 10 nanometers.

The term 'oxide' hereinafter refers to any inorganic oxide such as ZnO, MgO, CuO, and the like. In the following when ZnO is used specifically, it is used in exemplary fashion and can be replaced by any oxide as will be obvious to one skilled in the art.

The term 'plurality' refers hereinafter to any positive integer e.g, 1, 5, or 10.

It is within provision of the instant invention to offer a new process for preparation of surfaces and materials impregnated with nanometric oxide particles. The sonochemical method is applied for the deposition of ZnO nanocrystals on textile materials to impart them excellent antimicrobial activity. A comparison of the suggested ZnO-textile nanocomposite shows a clear advantage of the ultrasound radiation over all other available methods as will be described below.

We have demonstrated that sonochemical irradiation is a suitable method for synthesis of nanomaterials, and their deposition/insertion on/into ceramic, polymer, and other supports. One of the many advantages demonstrated for sonochemistry is that a homogeneous dispersion of the nanoparticles on the surface of the substrate is achieved in one step. In this step the nanoparticles of the desired products are formed and accelerated onto/into the surface or body of the polymer or ceramics via microjets or shock waves that are created when a sonochemically produced bubble collapses near a solid's surface. The current patent is based on the work done by the inventors—see *The Preparation of Metal-Polymer Composite Materials using Ultrasound Radiation*, S. Wizel, R. Prozorov, Y. Cohen, D. Aurbach, S. Margel, A. Gedanken. J. Mater. Res. 13, (1998) 211; *Preparation of amorphous magnetite nanoparticles embedded in polyvinylalcohol using ultrasound radiation*". R. Vijaykumar, Y. Mastai, A. Gedanken, Y. S. Cohen, Yair Cohen, D. Aurbach, J. Mater. Chem. 10 (2000) 1125; *Sonochemical Deposition of Silver Nanoparticles on Silica Spheres* V. G. Pol, D. Srivastava, O. Palchik, V. Palchik, M. A. Slifkin, A. M. Weiss. A. Gedanken, Langmuir, 18, (2002) 3352; *Synthesis and Characterization of Zinc Oxide-PVA Nanocomposite by Ultrasound Irradiation and the Effect of the Crystal Growth of the Zinc Oxide*" R. Vijayakumar, R. Elgamiel, O. Palchik, A. Gedanken, J. Crystal Growth and Design, 250 (2003) 409; *Sonochemical Deposition of Silver Nanoparticles on Wool Fibers*. L. Hadad, N. Perkas, Y. Gofer, J. Calderon-Moreno, A. Ghule, A. Gedanken. J. Appl. Polym. Sci. 104 (2007) 1732. These publications studied the deposition of large variety of nanoparticles on different kinds of substrates. The deposition was conducted either with materials that were dissolved in the irradiated solution or dispersed (not dissolved) in the solution.

The use of the sonochemical method helps to achieve all the principal requirements of the antimicrobial surface coated with nanomaterials: small particle size, regular shape, and homogeneous distribution of ZnO nanoparticles on the surfaces. Amongst the advantages of using ultrasound over other methods is that ultrasonic shockwaves effectively blast the oxide nanocrystals onto a surface at such speed that it causes local melting of the substrate, guaranteeing firm embedding of the nanocrystals within the surface (e.g. textile fibers). Textiles and other surfaces sonochemically impregnated with ZnO display outstanding antimicrobial activity in the case of both gram-positive and gram-negative bacteria.

Experimental procedures were developed as follows for testing and evaluation purposes. Other routes will be obvious to one skilled in the art, and the following is provided only by way of example.

Preparation Procedure
1. A sample (such as a cotton square of about 100 $cm^2$) is placed in a 0.002-0.02 M solution of $M(Ac)_2$, (where M stands for metals Zn, Mg, Cu; and Ac stands for acetate ion) in a water:ethanol (1:9) solution.
2. The pH is adjusted to 8 with an aqueous solution of ammonia.
3. The reaction mixture is then purged with argon for 1 hour in order to remove traces of $CO_2$/air.
4. The solution is irradiated for 1 hour with a high intensity ultrasonic horn (Ti-horn, 20 kHz, 1.5 kW at 70% efficiency) under a flow of argon at 30° C.
5. The textile is washed thoroughly with water to remove traces of ammonia, then further washed with ethanol and dried in air.

It is also within provision of the invention to prepare the metal solutions as above using metal nitrates or other salts, as will be obvious to one skilled in the art. Ethanol may also be excluded and water used in place of a water-ethanol solution.

As will also be obvious to one skilled in the art, the coating process can be accomplished without producing nanoparticles 'in house', by adding nanoparticles obtained by some other means to solution and ultrasonically treating as above in steps 2-5. The yield (amount of nanoparticles on the textile) in this case would be lower but enough to get antibacterial properties.

Results

A sample coated by the above process with MO was tested for its antibacterial properties with gram-positive (*S. aureusa*) and gram-negative (*E. coli*) cultures. Antibacterial effects were shown in treated textiles even at a coating concentration of less than 1%, for all metal oxides mentioned above (Zn, Mg, Cu). We observed 98% reduction of the two strains of the bacteria after 1 hour. A sample coated by the above process but using water rather than a water-ethanol solution resulted in a complete killing within 30 minutes of treatment of both gram-positive *S. aureus* and gram-negative *E. coli* bacteria.

This is supported by the following table of results measuring bacteria reduction for two bacteria types (*E. coli* and *S. aureusa*) after various treatment times, for different particle sizes of ZnO crystallites. Sample ZnO-1 has diameter ~8 nm, sample ZnO-2 has diameter ~275 nm, and sample ZnO-3 has diameter ~600 nm.

TABLE 1 bacteria population reduction for different grainsizes and treatment times.

| Sample | Duration of treatment [h] | *E. coli* [CFU mL$^{-1}$] | $N/N_0$ | % Reduction in viability | *S. aureus* [CFU mL$^{-1}$] | $N/N_0$ | % Reduction in viability |
|---|---|---|---|---|---|---|---|
| ZnO-1 | 0 | $6.5 \times 10^7$ | 1 | 0 | $1.2 \times 10^7$ | 1 | 0 |
|  | 1 | $5.2 \times 10^6$ | $8.0 \times 10^{-2}$ | 92 | $3.5 \times 10^6$ | $2.9 \times 10^{-1}$ | 71 |
|  | 2 | $6.5 \times 10^5$ | $1.0 \times 10^{-2}$ | 99 | $2.0 \times 10^6$ | $1.7 \times 10^{-1}$ | 83 |
|  | 3 | $1.3 \times 10^5$ | $2.0 \times 10^{-3}$ | 99.8 | $2.4 \times 10^5$ | $2.0 \times 10^{-2}$ | 98 |
| ZnO-2 | 0 | $6.5 \times 10^7$ | 1 | 0 | $1.2 \times 10^7$ | 1 | 0 |
|  | 1 | $1.0 \times 10^7$ | $1.6 \times 10^{-1}$ | 84 | $6.4 \times 10^6$ | $5.3 \times 10^{-1}$ | 47 |
|  | 2 | $3.3 \times 10^6$ | $5.1 \times 10^{-2}$ | 95 | $4.1 \times 10^6$ | $3.4 \times 10^{-1}$ | 66 |
|  | 3 | $3.3 \times 10^5$ | $2.0 \times 10^{-3}$ | 99.5 | $1.3 \times 10^6$ | $1.1 \times 10^{-1}$ | 89 |
| ZnO-3 | 0 | $6.5 \times 10^7$ | 1 | 0 | $1.2 \times 10^7$ | 1 | 0 |
|  | 1 | $2.0 \times 10^7$ | $3.1 \times 10^{-1}$ | 69 | $1.0 \times 10^7$ | $8.7 \times 10^{-1}$ | 13 |
|  | 2 | $1.69 \times 10^7$ | $2.6 \times 10^{-1}$ | 74 | $8.2 \times 10^6$ | $5.8 \times 10^{-1}$ | 42 |
|  | 3 | $8.5 \times 10^5$ | $21.3 \times 10^{-1}$ | 87 | $3.8 \times 10^6$ | $3.2 \times 10^{-1}$ | 68 |

Our experiments have also demonstrated that antibacterial treatment of ZnO coated bandages can increase the sensitivity of bacteria cells to two kinds of antibiotics; a 43% additional reduction in colonies was detected for Chloramphenicol due to the metal oxide and 34% for Ampicillin. The concentrations of antibiotics used in these experiments were much lower than those normally expected to cause any significant change in the bacteria growth. Thus, our results indicate a cooperative or synergic effect of metal oxide textile impregnation and antibiotic treatment.

The textile composite so produced contains on the order of 1 wt % of metal oxide (MO). The MO nanocrystals are of size ~150 nm, and are homogeneously distributed on the surfaces of the textile fibers.

The metal oxide concentration in the fabrics prepared as above can be varied in the range 0.5-10.0%.

Similar metal oxide concentration wt %, nanocrystal size, and distribution homogeneity in the fabrics prepared are obtained with the use of water rather than water-ethanol solution.

Figure 2A:
FIG. 2A-C presents HR SEM images of the fabric coated with ZnO: a—before coating, b—after coating, c—high magnification of figure b.
Figure 2B:
Figure 2C:
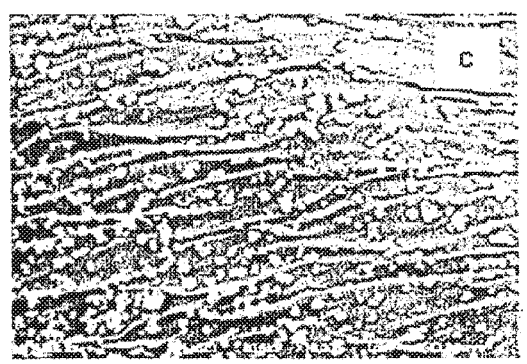
Figures 3A, 3B:
FIG. 3A, B present images of fabric coated with ZnO: a—before coating, b—after coating.

We now refer to FIG. 1 which displays XRD patterns of fabrics coated with zinc oxide, confirming the presence of ZnO nanocrystals. The homogeneous distribution of ZnO nanocrystals on the textile fibers was demonstrated in high-resolution SEM micrographs (FIG. 2). After sonochemical deposition of ZnO nanocrystals on the fabrics the color and texture of the material didn't change (FIG. 3).

Figure 4A:
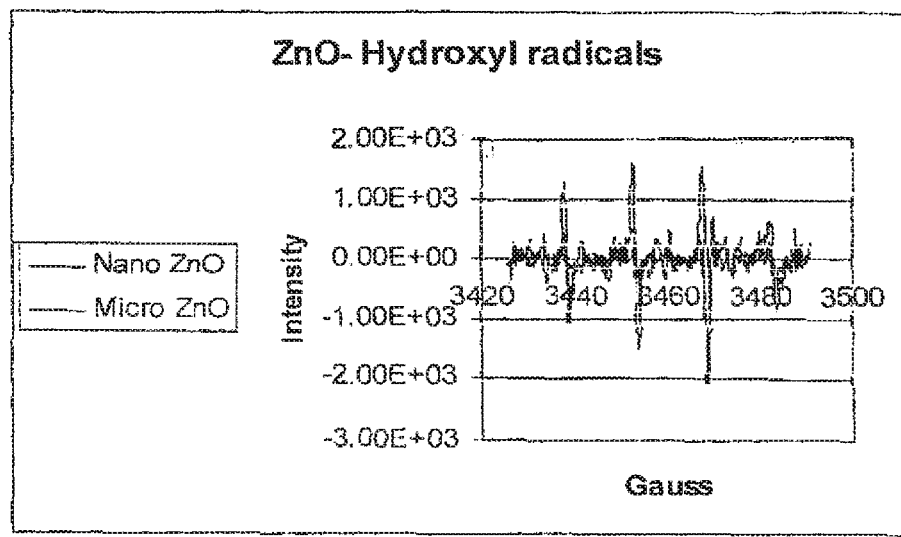
FIG. 4A, B presents a Comparing hydroxyl radicals generated from microscale and nanoscale ZnO, using DMPO as a spin-trapping agent and Theoretical (Computer) simulation of the ESR spectrum of hydroxyl radicals.
Figure 4B:
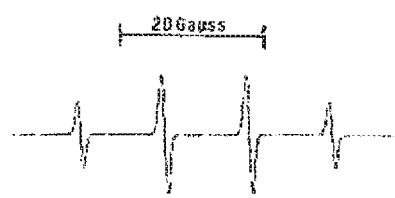

As is known in the art, the existence of free radicals can aid in destruction of bacteria. In our investigation, the generation of both active oxygen species ($O_2^-$ and $OH^-$) from the ZnO powder was demonstrated using ESR measurements. Moreover, we found that at the nanoscale regime of ZnO particle size, the amount of the generated $OH^-$ was considerably higher than that of the microscale size, probably due to a higher specific surface area of the smaller particles (FIG. 4). Similar spectra were obtained when a piece of ZnO-cotton coated bandage was introduced in the ESR tube. These results are in good agreement with the measured influence of particle size on the antibacterial activity of ZnO powders, as it was found that the antibacterial activity of ZnO increased with decreasing particle size.

Figure 6:
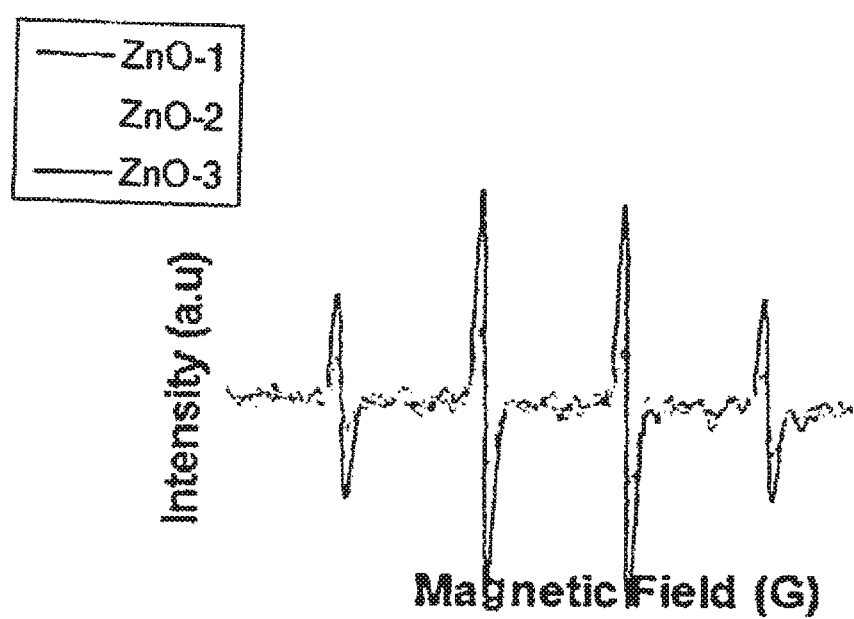
FIG. 6 presents ESR hydroxyl radical spectra of water suspensions with different ZnO samples, showing clearly that as the grainsize decreases the hydroxyl signal increases.

As is clear from the table above, the bacteria populations are reduced with greater exposure time and smaller ZnO grain size. The above explanation for these results is further substantiated in FIG. 6 which presents ESR hydroxyl radical spectra of water suspensions with different ZnO samples, showing clearly that as the grainsize decreases the hydroxyl signal increases.

The textiles sonochemically impregnated with ZnO demonstrate high stability; the amount of ZnO remaining in the textile after 50 washing cycles remains constant. The stability of nanoparticles on the fabric was measured after 50 washing cycles by both TEM measurements, and titrating the fabric with EDTA to determine the amount of ZnO.

Figure 5:
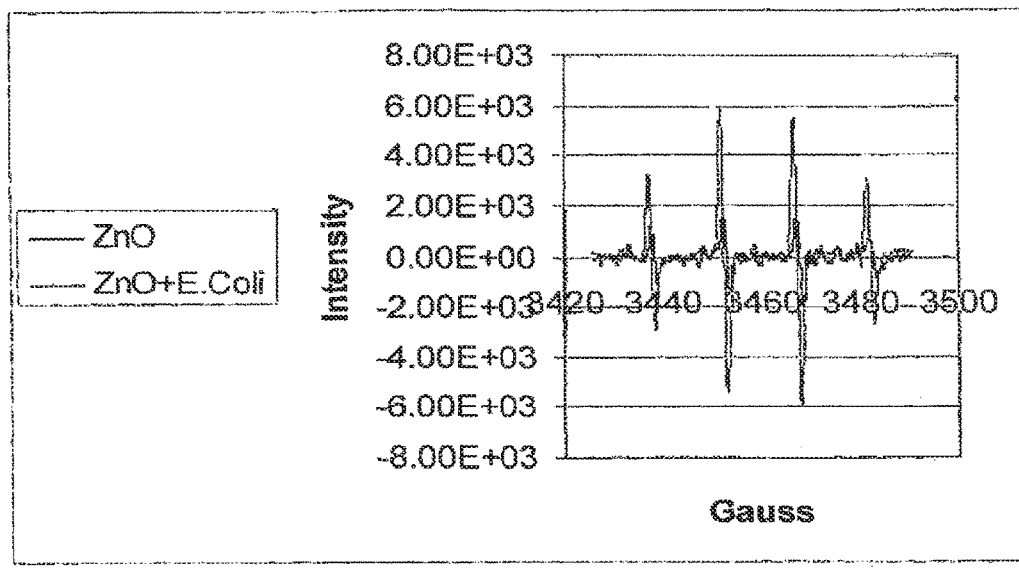
FIG. 5 presents the amount of the hydroxyl radicals in a medium containing both ZnO and bacteria.

In another experiment, we measured the amount of the hydroxyl radicals in a medium containing both ZnO and bacteria (*e. coli* and *s. aureusa* in saline). An enhancement of the amount of hydroxyl radicals could be detected comparing to samples without the bacteria (FIG. 5). We assume that this enhancement comes from an oxidative stress of the bacteria in a medium containing the ZnO.

What is claimed is:

1. A method comprising:
   immersing a surface in a mixture of metal acetate (M(AC) 2) added to a solution;
   adjusting a pH of the mixture to a range of about 8-10; and
   ultrasonically irradiating the mixture via ultrasonic waves, the ultrasonic waves
      (i) sonochemically causing bubbles to form in the mixture; and
      (ii) sonochemically causing the bubbles to collapse,
   wherein the collapsing of the bubbles:
      create metal oxide (MO) nanoparticles from the M(AC) 2; and
      form microjets near the surface that embed the MO nanoparticles into the surface.

2. The method of claim 1, wherein the solution comprises water and a solvent.

3. The method of claim 2, wherein the solvent comprises ethanol.

4. The method of claim 1, wherein the pH is adjusted by addition of a basic material.

5. The method of claim 4, wherein the basic material is ammonia.

6. The method of claim 1, wherein the ultrasonic irradiation is at a frequency of approximately 20 kHz.

7. The method of claim 1, wherein M is selected from a group consisting of metals Zn, Mg, Cu and any combination thereof.

8. The method of claim 1, wherein the irradiating is carried out for 1 hour.

9. The method of claim 1, wherein the irradiating is performed under a flow of argon.

10. The method of claim 1, wherein the irradiating is carried out at approximately 30° C.

11. The method of claim 1, wherein the surface contains between 0.1 wt % and 10 wt % of metal oxide (MO).

12. The method of claim 1, further comprising purging the mixture to remove traces of $CO_2$ or air.

13. The method of claim 12, wherein the purging is carried out with argon for 1 hour.

14. The method of claim 1, wherein a concentration of the metal acetate M(AC)2 is between 0.002 M to 0.2 M, and wherein the formed MO nanoparticles have diameters of between 1 nm and 1000 nm.

15. The method of claim 1, wherein the MO nanoparticles are embedded so that they are about equally distributed on the surface.

16. The method of claim 4, further comprising:
a. removing the surface from the mixture;
b. removing the basic material from the surface by washing the surface with water; and
c. washing the surface with ethanol.

17. A method, comprising:
immersing a surface in a mixture of metal acetate (M(AC)2) added to water;
adjusting a pH of the mixture to a range of about 8-10; and
ultrasonically irradiating the mixture via ultrasonic waves, the ultrasonic waves
(i) sonochemically causing bubbles to form in the mixture; and
(ii) sonochemically causing the bubbles to collapse,
wherein the collapsing of the bubbles:
create metal oxide (MO) nanoparticles from the M(AC)2; and
form microjets near the surface that embed the MO nanoparticles into the surface.

18. The method of claim 17, wherein M is selected from a group consisting of metals Zn, Cu and any combination thereof.

19. A method, comprising:
immersing a surface in a liquid mixture comprising metal acetate (M(AC)2);
adjusting a pH of the mixture to a range of about 8-10; and
ultrasonically irradiating the mixture via ultrasonic waves, the ultrasonic waves
(i) sonochemically causing bubbles to form in the mixture; and
(ii) sonochemically causing the bubbles to collapse,
wherein the collapsing of the bubbles:
create metal oxide (MO) nanoparticles from the M(AC)2; and
form microjets near the surface that embed the MO nanoparticles into the surface.

20. A method, comprising:
immersing a surface in a mixture comprising metal oxide (MO) nanoparticles;
adjusting a pH of the mixture to a range of about 8-10; and
ultrasonically irradiating the mixture via ultrasonic waves at a frequency of approximately 20 kHz, the ultrasonic waves
(i) sonochemically causing bubbles to form in the mixture; and
(ii) sonochemically causing the bubbles to collapse,
wherein the collapsing of the bubbles form microjets near the surface that embed MO nanoparticles in the mixture onto the surface.

21. A method, comprising:
immersing a surface in a mixture comprising metal acetate (M(AC)2);
forming metal oxide (MO) nanoparticles by adjusting a pH of the mixture to a range of about 8-10; and
ultrasonically irradiating the mixture via ultrasonic waves at a frequency of approximately 20 kHz, the ultrasonic waves
(i) sonochemically causing bubbles to form in the mixture; and
(ii) sonochemically causing the bubbles to collapse,
wherein the collapsing of the bubbles form microjets near the surface that embed the MO nanoparticles into the surface.

22. A method, comprising:
immersing a surface in a mixture comprising metal acetate M(AC)2;
adjusting a pH of the mixture to a range of about 8-10; and
sonochemically forming bubbles in the mixture by ultrasonically irradiating the mixture with ultrasonic waves at a frequency of approximately 20 kHz; and
sonochemically causing the bubbles to collapse so as to form microjets near the surface, the microjets embedding MO nanoparticles in the mixture onto the surface.

* * * * *